United States Patent
Debon et al.

(10) Patent No.: US 11,441,016 B2
(45) Date of Patent: *Sep. 13, 2022

(54) NATURAL EQUIVALENT OF CHEMICALLY MODIFIED STARCH

(71) Applicants: Cargill, Incorporated, Wayzata, MN (US); Alexander M. Lodge, Wayzata, MN (US)

(72) Inventors: Stephane Jules Jerome Debon, Denderleeuw (BE); Jozef Guido Roza Vanhemeirijck, Meise (BE); Bernd Wolfgang Kettlitz, Bonheiden (BE)

(73) Assignee: Cargill, Incorporated, Wayzata, MN (US)

( * ) Notice: Subject to any disclaimer, the term of this patent is extended or adjusted under 35 U.S.C. 154(b) by 857 days.

This patent is subject to a terminal disclaimer.

(21) Appl. No.: 16/161,520

(22) Filed: Oct. 16, 2018

(65) Prior Publication Data
US 2019/0048170 A1 Feb. 14, 2019

Related U.S. Application Data

(62) Division of application No. 12/516,157, filed as application No. PCT/EP2007/062739 on Nov. 23, 2007, now Pat. No. 10,131,771.

(30) Foreign Application Priority Data

Nov. 23, 2006 (EP) .................................... 06124634

(51) Int. Cl.
| | | |
|---|---|---|
| *C08L 3/02* | (2006.01) | |
| *A23L 23/00* | (2016.01) | |
| *A23L 33/22* | (2016.01) | |
| *A23L 19/00* | (2016.01) | |
| *A23L 29/269* | (2016.01) | |
| *A23L 2/52* | (2006.01) | |
| *A23L 29/212* | (2016.01) | |
| *C08L 97/02* | (2006.01) | |

(52) U.S. Cl.
CPC .................... *C08L 3/02* (2013.01); *A23L 2/52* (2013.01); *A23L 19/00* (2016.08); *A23L 23/00* (2016.08); *A23L 29/212* (2016.08); *A23L 29/269* (2016.08); *A23L 29/27* (2016.08);
(Continued)

(58) Field of Classification Search
None
See application file for complete search history.

(56) References Cited

U.S. PATENT DOCUMENTS

| | | |
|---|---|---|
| 4,225,628 A | 9/1980 | Lynn et al. |
| 4,503,083 A | 3/1985 | Glicksman et al. |

(Continued)

FOREIGN PATENT DOCUMENTS

| | | |
|---|---|---|
| EP | 1038882 A1 | 9/2000 |
| EP | 1159880 A2 | 12/2001 |

(Continued)

OTHER PUBLICATIONS

"JP 04-030765", J-PlatPat, Feb. 3, 1992, 1-3.
(Continued)

*Primary Examiner* — Jenna A Watts

(57) ABSTRACT

The present invention relates to a composition comprising citrus fruit fiber having a water binding capacity of from 8 to 25 (w/w) and native starch selected from the group consisting of corn starch, rice flour, sorghum starch, tapioca starch and mixture thereof.

16 Claims, 1 Drawing Sheet

(52) U.S. Cl.
CPC .............. *A23L 33/22* (2016.08); C08L 97/02 (2013.01); *A23V 2002/00* (2013.01)

(56) References Cited

U.S. PATENT DOCUMENTS

| | | | |
|---|---|---|---|
| 4,526,794 | A | 7/1985 | Altomare et al. |
| 4,865,863 | A | 9/1989 | Prosise et al. |
| 5,538,751 | A | 7/1996 | Carter et al. |
| 2003/0152667 | A1 | 8/2003 | Goedeken et al. |
| 2005/0074542 | A1 | 4/2005 | Lundberg et al. |
| 2005/0089621 | A1 | 4/2005 | Aquino et al. |
| 2009/0035441 | A1 | 2/2009 | Hirashima et al. |

FOREIGN PATENT DOCUMENTS

| | | | |
|---|---|---|---|
| EP | 1723856 | A1 | 11/2006 |
| JP | 04030765 | A | 2/1992 |
| JP | H05507845 | A | 11/1993 |
| JP | H07506493 | A | 7/1995 |
| JP | 09299051 | A | 11/1997 |
| JP | H09299051 | A | 11/1997 |
| JP | 2002300866 | A | 10/2002 |
| WO | WO-2006033697 A1 * | 3/2006 | ........... A23L 13/426 |

OTHER PUBLICATIONS

Larrea, M. A., et al., "Some functional properties of extruded orange pulp and its effect on the quality of cookies", Lebensmittel Wissenschaft Und Technologie, 38(3), May 2005, 213-220.

Robertson, Karen, "Gluten-free Flour Alternatives", Celiac.com, Jan. 11, 2005, 1-2.

Thomas, David J., "Starches", Eagan Press Handbook Series, American Association of Cereal Chemists, St. Paul, Minnesota, 1999, 25-30.

* cited by examiner

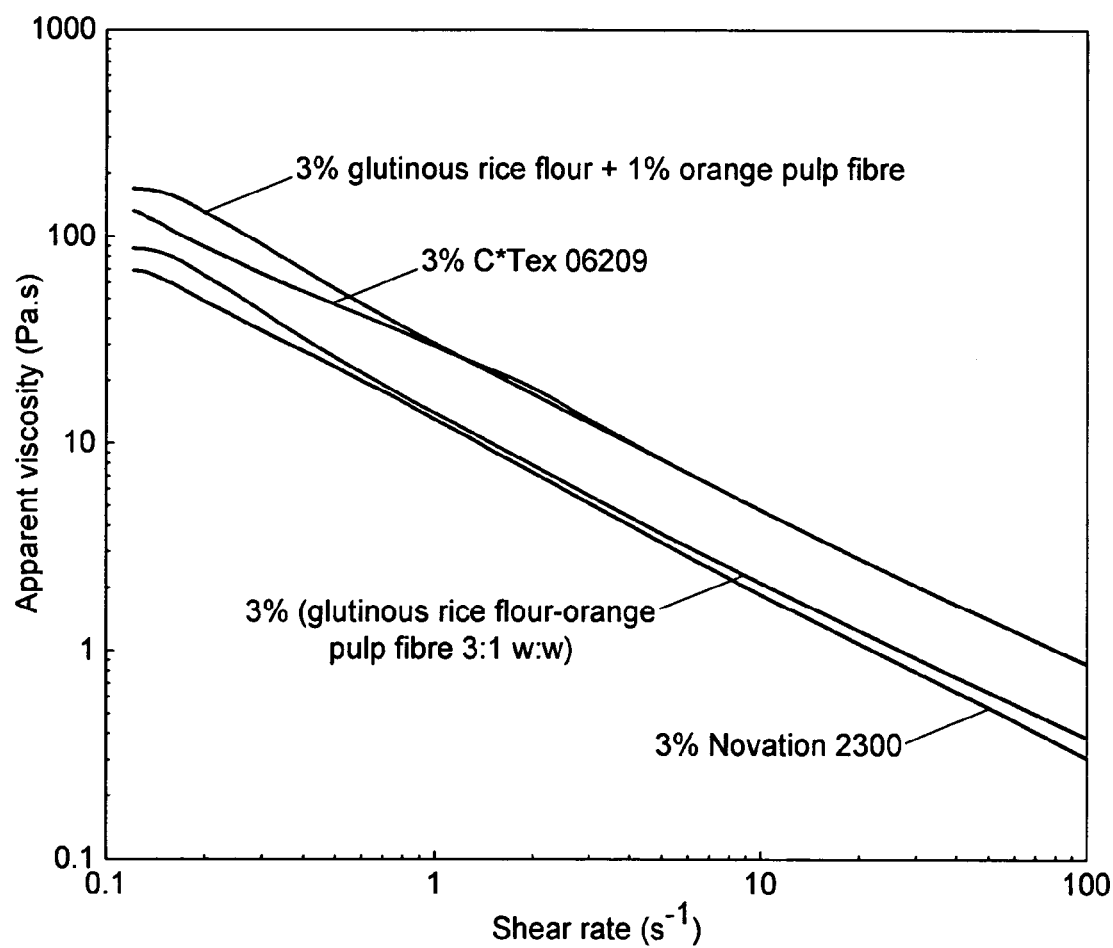

NATURAL EQUIVALENT OF CHEMICALLY MODIFIED STARCH

CROSS-REFERENCE TO RELATED APPLICATIONS

This application is a Division of application Ser. No. 12/516,157, filed on Dec. 22, 2009, now U.S. Pat. No. 10,131,771, and entitled NATURAL EQUIVALENT OF CHEMICALLY MODIFIED STARCH, which claims the benefit of PCT Patent Application No. PCT/EP07/062739, filed Nov. 23, 2007, and entitled NATURAL EQUIVALENT OF CHEMICALLY MODIFIED STARCH, which application claims priority to European Provisional Application No. 06124634.4, filed Nov. 23, 2006, and entitled NATURAL EQUIVALENT OF CHEMICALLY MODIFIED STARCH which applications are hereby incorporated by reference herein in their entirety.

TECHNICAL FIELD

The current invention relates to an edible substitute for chemically modified starch. It further relates to a process for preparing said substitute which comprises citrus fibers and native starch. Finally, the present invention pertains to the use of citrus fiber and native starch as a natural alternative to chemically modified starch.

BACKGROUND OF THE INVENTION

Food manufacturers are continuously challenged to find ways to present an appetizing and authentic food product at minimized raw material costs. One area of particular endeavor has been the goal of producing compositions including fully natural ingredients. Particularly, the consumer demands for foods containing starches which have not been chemically modified but which have the same functional properties as chemically modified starches.

Indeed, starches are often chemically modified with different reagents to produce starches having, for example, excellent tolerance to processing variables such as heat, shear, pH extremes, and storage stability. Such chemically modified starches provide interalia a desirable smooth texture and possess viscosity stability throughout the processing operation and normal shelf life of the food. In contrast, unmodified starches breakdown in viscosity, loose thickening capacity and textural qualities, and behave unpredictably during storage as a result of the stresses encountered during food processing. Heat, shear, and/or an extreme pH, especially an acidic pH, tend to fully disrupt the starch granules and disperse the starch polymers into the food. Hence, unmodified starches also called native starches are generally unsuitable for use in processed foods.

Different solutions have already been proposed in the art to address this issue, for example, in EP 721 471 and EP 1 038 882 thermally inhibited starches and flours that are functionally equivalent to chemically modified (i.e., cross-linked) starches are disclosed.

EP 830 379 and 1 159 880 relate to pregelatinized non-granular starches that are inhibited in order to have the textural properties of chemically crosslinked pregelatinized non-granular starches. In these references, the "physically" modified starches described do not contain chemical modifications but their structure is modified during the process.

Another solution that has been proposed in the art is to fully replace chemically modified starch by citrus fiber in low fat emulsions. This solution seems to be satisfactory, even if some grittiness appears, as citrus fiber is a highly functional texturizing material but citrus fiber suffers from being relatively expensive.

Accordingly, there is still a need for having a low cost natural ingredient exhibiting the same functionality than chemically modified starch. The present invention fulfills this need by providing a composition comprising citrus fiber and native starch, its use as edible substitute for chemically modified starch, and a process for preparing it. Indeed, the inventors have surprisingly found that mixing citrus fiber with native starch results in a product having process tolerance required in the food industry, such as resistance to shear, as well as improved texture, and freeze thaw stability.

SUMMARY OF THE INVENTION

The current invention relates to a composition suitable to substitute chemically modified starch comprising citrus fiber having a water binding capacity of from 7 to 25 (w/w) and native starch selected from the group consisting of corn starch, rice flour, sorghum starch, tapioca starch, waxy wheat flour, amylase free potato starch and mixture thereof. In a preferred embodiment, the starch used is a waxy starch.

Also part of this invention is a composition where the ratio of citrus fruit fiber to native starch is from about 1:10 to about 2:1.

The citrus fiber, in the present invention, is having a total dietary fiber content of from 60 to 85-wt % (dry weight) and a water binding capacity of from 7 to 25 (w/w). The citrus fiber can comprise up to 12% (w/w) proteins. Furthermore the citrus fiber is obtainable from citrus fruit selected from the group consisting of oranges, tangerines, limes, lemons and grapefruit. In a preferred embodiment the citrus fiber used is orange pulp fiber.

The composition according to the invention may further comprise edible additives and for example xanthan gum, guar gum, pectin, carrageenan, fiber, soy protein and mixtures thereof.

The present invention also relates to a process for preparing the composition of the present invention where a blend of citrus fiber and native starch is prepared and then treated mechanically in order to homogenized the blend to form a mixture; after that the mixture is cooked up to the gelatinization temperature of the starch under stirring.

The currently disclosed invention is suitable to be used in food applications, feed applications, pharma products or cosmetics. Sauces and soups containing the composition of the present invention are preferred embodiments. The amount of the composition according to the present invention in the final product is preferably from about 2 to about 6 percent by weight.

BRIEF DESCRIPTION OF THE DRAWING

FIG. 1 is a comparative example of the behaviors of a chemically modified starch (C*Tex 06209), a thermally inhibited starch (Novation 2300) and a composition according to the invention (citrus fiber and native starch) when measured in rotational mode.

DETAILED DESCRIPTION

The current invention relates to a composition suitable to substitute chemically modified starch comprising citrus fiber having a water binding capacity of from 7 to 25 (w/w) and native starch selected from the group consisting of corn starch, glutinous rice flour, sorghum starch, tapioca starch, waxy wheat flour, amylase free potato starch and mixture thereof. In a preferred embodiment, the native starch is a waxy starch and particularly glutinous rice flour.

The citrus fiber, used in the present invention, is a valuable component having relatively high total dietary fiber content and a balanced ratio of soluble to insoluble dietary fiber. For example, the total dietary fiber preferably is made up of about 45-50% soluble dietary fiber and from 50-55% insoluble dietary fiber. The balanced dietary fiber spectrum insoluble (structural) and soluble (chiefly pectin) fiber is advantageous in physiological functionality over cereal-based fibers. Citrus fiber, particularly orange fiber, more in particular dried citrus fiber; has an extremely high water binding capacity, resulting in high viscosities compared to other citrus fibers such as Vitacel™ orange fiber (available from Rettenmaier). In one preferred embodiment, dried citrus fiber has a total dietary content of from about 60 to about 85-wt % (based on dry substance) and a water binding capacity from 7 to about 25 (w/w). Preferably the total dietary fiber content is at least about 70-wt % and the water binding capacity is at least about 8 (w/w), more preferably at least about 12, most preferably from 19 to 25. The protein content of the dried citrus fiber is up to 12, preferably from 8 to 12-wt %.

The citrus fiber is extracted from citrus vesicles from a wide variety of citrus fruits, non-limiting examples of which include oranges, tangerines, limes, lemons, and grapefruit.

Citrus vesicles refer to the cellulosic material contained in the inner, juice-containing portion of citrus fruit. Citrus vesicles are sometimes also referred to as coarse pulp, floaters, citrus cells, floating pulp, or pulp. In contrast, citrus flour obtained from citrus peel is characterized by an orange peel taste and odor, and a dark orange color, which is severely limiting the product's uses. Additional advantages of citrus fiber versus citrus flour are a higher total dietary fiber content (e.g., about 72-wt % versus 58-wt %); lower carbohydrate content (e.g., about 5-wt % versus 15-wt %); and higher water binding (e.g., greater than about 8.5 grams of water per gram of fiber versus 5.5 g/g).

The ratio soluble to insoluble dietary fiber is an important factor in the citrus fiber's functionality. Other important considerations include the degree of milling (granulometry) and drying conditions (process of drying). Generally, a higher degree of milling (i.e., a finer fiber granulometry) results in more smoothness of the fiber in the solution, as well as reduced water absorption capacity and reduced oil binding capacity compared to coarse fibers. Preferably dried citrus fruit fiber is obtainable according to the process disclosed in the pending patent application WO 2006/033697. In a preferred embodiment, the citrus fiber is orange fiber having a water binding capacity of from 12 to 25, preferably from 19 to 25. Said orange fiber has preferably an oil binding capacity of from 2 to 10, preferably from 4 to 10, more preferably from 5 to 9.

Without being bound by any theory, it is believed, according to the present invention, that the citrus fiber when included in the present inventive combination and then further processed is acting as a protective agent for the starch. Indeed, the resistance of said starch is increased, particularly when treated with shear forces. It is believed that this higher resistance is due to starch granule swelling inhibition allowed by the citrus fiber. According to the present invention, the more the fiber binds water and oil the more the starch will be protected by said fiber.

A preferred version of the invention involves an orange fiber having a water binding capacity of 19 to 25, an oil binding capacity of from 5 to 9 in combination with glutinous rice flour.

Also part of this invention is a composition where the weight ratio of citrus fruit fiber to native starch is from about 1:10 to about 2:1, preferably from 1:7 to 1:1, more preferably from 1.5 to 1:3.6, and most preferably from 1:5 to 1:2.

Said composition can further comprise edible additives. These edible additives are selected from the group consisting of carbohydrates, gums, proteins, peptides, amino acids, pectins, antioxidants, trace elements, electrolytes, intense sweeteners, edible acids, flavors, barley beta-glucans, colorants, preservatives, and mixtures thereof.

The carbohydrates are selected from the group consisting of monosaccharides, disaccharides, oligosaccharides, dextrins, fibers, starch hydrolysates, polyols and mixtures thereof. The monosaccharides include tetroses, pentoses, hexoses and ketohexoses.

Typical disaccharides include sucrose, maltose, trehalulose, melibiose, kojibiose, sophorose, laminaribiose, isomaltose, gentiobiose, cellobiose, mannobiose, lactose, leucrose, maltulose, turanose and the like.

Starch hydrolysates are produced by the controlled acid or enzymatic hydrolysis of starch and can be subdivided into two specific categories, maltodextrins and glucose syrups and are characterized by DE number (dextrose equivalent). In fact, DE number is a measurement of the percentage of reducing sugars present in the syrup and calculated as dextrose on a dry weight basis. Maltodextrins have a DE (dextrose equivalent) number up to 20 whereas glucose syrups have an DE number greater than 20.

Dextrins are prepared according to the dextrinisation method. Dextrinisation is a heat treatment of dry starch in presence or absence of acid.

The low-calorie fibers can be polydextrose, arabinogalactan, chitosan, chitin, xanthan, pectin, cellulosics, konjac, gum Arabic, soy fiber, inulin, hydrolysed guar, guar gum, beta-glucan, carageenan, locust bean gum, alginate, polyglycol alginate.

Among the major physiological electrolytes are sodium, potassium, chloride, calcium, and magnesium. Further trace elements can be included such as chromium, copper, selenium, iron, manganese, molybdenum, zinc and mixtures thereof.

The edible acids can be selected from phosphoric acid, citric acid, malic acid, succinic acid, adipic acid, gluconic acid, tartaric acid, fumaric acid and mixtures thereof.

An intense sweetener, which can be used as non-nutritive sweetener can be selected from the group consisting of aspartame, acesulfame salts such as acesulfame-K, saccharins (e.g. sodium and calcium salts), cyclamates (e.g. sodium and calcium salts), sucralose, alitame, neotame, steviosides, glycyrrhizin, neohesperidin dihydrochalcone, monatin, monellin, thaumatin, brazzein and mixtures thereof.

The flavors are selected from fruit flavors, botanical flavors and mixtures thereof. Preferred flavors are cola flavor, grape flavor, cherry flavor, apple flavor and citrus flavors such as orange flavor, lemon flavor, lime flavor, fruit punch and mixtures thereof. The amount of flavor depends upon the flavor or flavors selected, the flavor impression desired and the form of flavor used.

If desired, coloring agents can also be added. Any coloring agent approved for food use can be utilized for the current invention.

When desired, preservatives such as potassium sorbate and sodium benzoate can be added.

In a preferred embodiment, the edible additive added is selected from the group consisting of xanthan gum, guar gum, pectin, carrageenan, fiber, soy protein and mixture thereof. In another embodiment, the preferred edible additive is xanthan gum.

The present invention also encompasses a process for preparing a composition comprising citrus fiber having a water binding capacity of from 7 to 25 (w/w) and native starch selected from the group consisting of corn starch, rice flour, sorghum starch, tapioca starch and mixture thereof.

Said process comprising the steps of:
a) Blending citrus fruit fibers and native starch,
b) Treating mechanically the blend of step a) to obtain a homogeneous mixture,
c) Cooking the mixture under gentle stirring up to the gelatinization temperature of the starch.

To form the blend of step a, any homogenization method can be used as the degree of hydration of the citrus fruit fiber is not highly critical.

Suitable mechanical treatment for step b) is treatment with high-shear mixers, high-pressure valve homogenization, microfluidisation, high-power ultrasound and the like. By applying a strong shearing force, such as for example a high-pressure valve homogenizer, less dense fibre particles and increased thickening can be obtained.

The mixture of step b) is then cooked to swell the starch granules. This will render the medium viscous; gentle stirring is used in order to homogenize the mixture, strong mechanical treatment should be avoided to not disrupt the starch granules.

The gelatinization temperature depends on the type of starch used; this should be determined by the skilled person; however gelatinization for some type of native starch can be found in the literature and for example in the book by David J. Thomas and Williams A. Atwell, Starches, Eagan Press Handbook Series, American Association of Cereal Chemists, St. Paul, Minn. (1999), pages 25-30.

Cited temperatures are as follow:

| Starch source | Gelatinization temperature (° C.) |
| --- | --- |
| Wheat | 52-85 |
| Tapioca | 52-65 |
| Waxy Corn | 63-72 |

The gelatinization temperature are given by ranges as it depends on the moisture content and the salt content of the medium.

The current invention relates to the use of the currently disclosed composition in food applications, feed applications, pharma products or cosmetics. Food applications may include beverages, dairy products, ice creams, sorbets and, desserts. Said beverages include concentrates, gels, energy drinks, and carbonated beverages, non-carbonated beverages, syrups. The beverage can be any medical syrup or any drinkable solution including iced tea, and fruit juices, vegetable based juices, lemonades, cordials, nut based drinks, cocoa based drinks, dairy products such as milk, whey, yogurts, buttermilk and drinks based on them. Beverage concentrate refers to a concentrate that is in liquid form. The liquid concentrate can be in the form of a relatively thick, syrupy liquid. Preferred application are soups, dressing, bakery products, low fat spreads and sauces. More preferred applications are béchamel sauces and tomato sauces.

The combination of the present invention is also suitable to be included in hot instant product like soups; in this case, the skilled person must envisage other kind of starches. Indeed, if the mixture has not been cooked before being included in the instant product, the consumer will have to face textural problem like sandiness. Thus to overcome this, pregelatinized starch e.g. spray cooked starch must be used.

Another possibility is to combine the citrus fiber with thermally inhibited starch for application to be submitted to extreme conditions (for example pH around 3.5 and temperature above 95° C.) or for application requiring extremely high viscosity.

In a preferred embodiment the combination according to the present invention is present in the final product in an amount of from about 1.5 to about 7-wt % of the composition, preferably from 2 to 6-wt %, and more preferably from 3 to 5-wt %.

The current invention has the following advantages:
1) The composition, comprising citrus fruit fiber and native starch, has a high nutritional value, is stable during the process and, allows positive food labeling.
2) Using native starch, which is a very cheap ingredient, permits to manufacture a low cost, highly efficient, and natural texturizing agent.
3) This composition is also useful for products requesting cold storage as the protective effect of the citrus fiber helps the stabilization of the starch even at low temperature.

The invention is further defined by reference to the following examples describing in detail the preparation of the composition of the present invention. The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

EXAMPLE

Example 1: Water and Oil Binding Capacity Analysis

The water binding (measured according to Protocol I) and oil binding capacity (measured according Protocol II) of orange pulp fiber (OPF) obtained by the process disclosed in WO2006/033697 were measured. The result were as follow:

| SAMPLES | WATER BINDNG CAPACITY g water/g product | OIL BINDING CAPACITY g water/g product |
| --- | --- | --- |
| OPF 40 µm | 19 | 5 |
| OPF 75 µm | 19 | 5 |
| OPF 250 µm | 24 | 9.5 |

As apparent the granulometry has an influence on both the water binding capacity and the oil binding capacity of the products. This experiment shows that depending on the result to be achieved, the skilled person could have to monitor the granulometry in order to bring more or less protective effect to the starch.

Example 2: Resistance of the Invention to Process Parameters (Shear Treatment)

A composition of orange pulp fiber and waxy cornstarch on one side and Orange pulp fiber (OPF) and cornstarch on the other side was formed and submitted to shear treatment. The shear treatment applied was 13500 rpm with Silverson mixer during 1.5 minute.

All the viscosity measurements have been made using a Brookfield with a cylindrical spindle (62) at 10 rpm during 20 seconds.

The results are apparent in the following table:

| Material | Before treatment (mPA · s) | After treatment (mPa · s) |
|---|---|---|
| Cornstarch (2.5%) + OPF (4%) | 116 000 | 105 000 |
| Cornstarch (4%) + OPF (2.5%) | 76 300 | 69 200 |
| Waxy cornstarch (2.5%) + OPF (4%) | 78 100 | 73 200 |
| Waxy cornstarch (4%) + OPF (2.5%) | 55 300 | 51 200 |

As apparent the combination of the invention is shear resistant as its values before and after treatment are almost the same.

Example 3: Preparation of a Sauce

Three sauces were prepared with the following recipe:

| Ingredients | Weight (g) | Composition (w % as is) |
|---|---|---|
| Sunflower oil | 75 | 10.0 |
| Skimmed milk powder | 30 | 4.0 |
| Egg yolk powder | 11 | 1.5 |
| Thickeners* | 22.5 | 3.0 |
| Salt | 3 | 0.4 |
| Demi-water | 608 | 81.1 |
| TOTAL | 750 | 100.0 |

*The thickeners tested were: the composition according to the invention: glutinous rice flour and Orange pulp fiber (ratio 3:1) a thermally inhibited stach: NOVATION 2300 a chemically modified starch: C*Tex 06209

The rheology of the different sauces was measured at 60° C. (rotation=FIG. 1).

As apparent from FIG. 1, the combination according to the invention is as good as thermally inhibited starch that is used to replace chemically modified starch.

Another trial has been made with 3% native starch and 1% orange pulp fiber. In this case, the natural substitute can even compete with chemically modified starch per se.

Example 4: Descriptive Textural and Sensory Analysis of the Sauces after Cold Storage (5° C.)

Descriptive textural and sensory analysis of the sauces after cold storage (5° C.).

It was not possible to measure the syneresis for C*Tex 06209, Novation 2300, and glutinous rice flour/orange pulp fiber as all were below the detection limit.

Thus visual observation was used, the result can be found in the following table:

| | Water syneresis | Fat syneresis | Bulk appearance | Overall rating (scale −1 to +1) |
|---|---|---|---|---|
| Good scores | | | | |
| Glutinous rice flour/orange pulp fiber | No syneresis | No syneresis | Short, creamy | 0.7 |
| Medium scores | | | | |
| C*Tex 06209 | No syneresis | Little | Short, grainy | 0.3 |
| Bad scores | | | | |
| Novation 2300 | No syneresis | Fat globule on surface | Long | −0.3 |

When manufacturing sauces, one of the targets is to obtain a product which are short, creamy mouthfeel, and not being subject to syneresis for appearance and shelf-life stability.

As apparent from the table here above, the only product in the comparative example having the required features was the sauce containing the inventive combination.

Protocol I
Water Binding Capacity 3 samples were ground at different granulometry (40 μm, 75 μm, and, 250 μm) and then weighted with a precision balance Sartorius CP 3245. Each sample was prepared in double and an average was made to give the final result.

The procedure was as follow:
In a 50 ml centrifuge tube, 0.5 g of the fiber (dry powder) was weighted (W1),
40 g milli-Q water was added. The weight of the water was noted (W2),
The tube was closed and stirred during 1 min by hand,
The tube was then submitted to a centrifugation during 5 min at 2000 rpm with the centrifuge Labofuge 400 Heraeus,
The supernatant was decanted and weighted (W3).
The water binding capacity (WBC) is expressed as g water/g sample:

$$WBC=(W2-W3)/W1$$

Protocol II
Oil Binding Capacity

The oil binding (OLB) of a product was determined by centrifugering a 5% powder dispersion and weighing the precipitate.

2 (independant) product dispersions were prepared by dispersing 2.5 g powder (W1) in 50 g (W2) soya-oil (standard quality) in a 300 ml beaker.

The samples were stirred for 10 minutes at about 500 rpm until the product was completely dispersed.

The samples were then left 30 minutes until the samples were adapted to the hydrophobicity.

The dispersions were stirred and for each sample a centrifuge tube with approximately 45 g product-in-oil dispersion was filled. The weight of the tube was noted as W3 and the total weight after filling the centrifuge tube with the dispersion was W4.

The tubes were centrifuged during 5 min at 3800 rpm with a Sorvall Automatic centrifuge SS-3. The supernatants were then decanted and the centrifuged tubes containing the precipitate were weighed again (W5).

The oil-binding capacity is expressed as g oil/g sample:

$$OLB = Wco/Wcp$$

| % product in start oil mixture | Wp = W1 × 100/(W1 + W2) |
| % oil in start oil mixture | Wo = W2 × 100/(W1 + W2) |
| Product weight | Wcp = (Wp/100) × (W4 − W3) |
| Oil bind | Wco = W5 − W3 − Wcp |

The invention claimed is:

1. A composition suitable to substitute chemically modified starch consisting of:
   citrus fruit fiber having a water binding capacity of from 7 to 25 grams of water per gram of fiber; and
   native starch selected from the group consisting of corn starch, rice flour, sorghum starch, tapioca starch, waxy wheat flour, amylase free potato starch and mixtures thereof
   wherein the weight ratio of citrus fruit fiber to native starch is in a range of from 1:5 and 1:1.

2. The composition according to claim 1, wherein the citrus fruit fiber is obtainable from citrus fruit selected from the group consisting of oranges, tangerines, limes, lemons, and grapefruit.

3. The composition according to claim 1, wherein the citrus fruit fiber has a total dietary fiber content of from 60 to 85-wt %.

4. The composition according to claim 1, wherein the citrus fruit fiber comprises from 8 to 12% (w/w) proteins.

5. The composition according to claim 1, wherein the native starch is a waxy starch.

6. The composition according to claim 5, wherein the native starch is glutinous rice flour.

7. A food application, feed application, pharmaceutical product and/or cosmetic comprising the composition according to claim 1.

8. A beverage comprising the composition according to claim 1.

9. A sauce comprising the composition according to claim 1.

10. The composition of claim 1, wherein the weight ratio of citrus fruit fiber to native starch is in a range of from 1:5 and 1:2.

11. A composition suitable to substitute chemically modified starch consisting of:
    citrus fruit fiber; and
    native starch selected from the group consisting of corn starch, rice flour, sorghum starch, tapioca starch, waxy wheat flour, amylase-free potato starch and mixtures thereof,
    wherein the citrus fruit fiber is fiber extracted from citrus vesicles which has a water-binding capacity of 7 to 25 grams of water per gram of fiber and a total dietary fiber content of 60 to 85 wt %, the total dietary fiber consisting of 45 to 50% soluble dietary fiber and 50 to 55% insoluble dietary fiber.

12. The composition of claim 11, wherein the weight ratio of citrus fruit fiber to native starch is in a range of from 1:5 and 1:1.

13. The composition of claim 11, wherein the citrus fruit fiber is obtainable from citrus fruit selected from the group consisting of oranges, tangerines, limes, lemons and grapefruit.

14. The composition of claim 11, wherein the citrus fruit fiber comprises from 8 to 12% (w/w) proteins.

15. The composition of claim 11, wherein native starch is a waxy starch.

16. The composition of claim 11, wherein the native starch is glutinous rice flour.

* * * * *